US011238958B2

(12) United States Patent
Leong et al.

(10) Patent No.: US 11,238,958 B2
(45) Date of Patent: Feb. 1, 2022

(54) SYSTEM FOR DETERMINING A COPY NUMBER OF A GENOMIC SEQUENCE

(71) Applicant: LIFE TECHNOLOGIES CORPORATION, Carlsbad, CA (US)

(72) Inventors: Harrison Leong, San Francisco, CA (US); Nivedita Sumi Majumdar, San Bruno, CA (US)

(73) Assignee: Life Technologies Corporation, Carlsbad, CA (US)

( * ) Notice: Subject to any disclaimer, the term of this patent is extended or adjusted under 35 U.S.C. 154(b) by 1007 days.

(21) Appl. No.: 14/807,764

(22) Filed: Jul. 23, 2015

(65) Prior Publication Data

US 2016/0026760 A1 Jan. 28, 2016

Related U.S. Application Data

(63) Continuation of application No. 13/689,374, filed on Nov. 29, 2012, now abandoned.

(60) Provisional application No. 61/564,503, filed on Nov. 29, 2011.

(51) Int. Cl.
*G16B 45/00* (2019.01)
*G16B 20/00* (2019.01)
*G16B 30/00* (2019.01)
*G16B 20/20* (2019.01)
*G16B 20/10* (2019.01)

(52) U.S. Cl.
CPC ............ *G16B 45/00* (2019.02); *G16B 20/00* (2019.02); *G16B 20/10* (2019.02); *G16B 20/20* (2019.02); *G16B 30/00* (2019.02)

(58) Field of Classification Search
None
See application file for complete search history.

(56) References Cited

U.S. PATENT DOCUMENTS

| | | | |
|---|---|---|---|
| 5,494,810 A | 2/1996 | Barany et al. | |
| 5,538,848 A | 7/1996 | Livak et al. | |
| 5,830,711 A | 11/1998 | Barany et al. | |
| 5,925,517 A | 7/1999 | Tyagi et al. | |
| 6,054,564 A | 4/2000 | Barany et al. | |
| 6,103,476 A | 8/2000 | Tyagi et al. | |
| 6,150,097 A | 11/2000 | Tyagi et al. | |
| 6,330,007 B1* | 12/2001 | Isreal .................... | G06F 3/0481 715/207 |
| 6,355,421 B1 | 3/2002 | Coull et al. | |
| 6,383,752 B1 | 5/2002 | Agrawal et al. | |
| 6,485,901 B1 | 11/2002 | Gildea et al. | |
| 6,548,250 B1 | 4/2003 | Sorge | |
| 6,589,250 B2 | 7/2003 | Schendel | |
| 6,589,743 B2 | 7/2003 | Sorge | |
| 6,590,091 B2 | 7/2003 | Albagli et al. | |
| 6,593,091 B2 | 7/2003 | Keys et al. | |
| 6,596,490 B2 | 7/2003 | Dattagupta | |
| 2009/0204660 A1* | 8/2009 | Chappell ............... | G06F 9/4484 709/201 |
| 2010/0228496 A1* | 9/2010 | Leong .................... | G06F 19/22 702/19 |

FOREIGN PATENT DOCUMENTS

WO 9921881 A1 5/1999

OTHER PUBLICATIONS

Klein et al. (Electrophoresis, 1999, vol. 20, p. 291-299). (Year: 1999).*
Huang (BMC Bioinformatics, 2006, 7:83, pp. 1-21). (Year: 2006).*
Applied Biosystems (CopyCaller Software, User Guide, Copyright 2009, pp. 1-82) (Year: 2009).*
Applied Biosystems (Copy Caller User Manual, v2.0, Nov. 2011, pp. 1-92) (Year: 2011).*
Tyagi, Sanjay, et al., Molecular Beacons: Probes that Fluoresce upon Hybridization, Nature Biotechnology, Mar. 1996, pp. 303-308, vol. 14.
Kubista, Mikael, et al., Light-up probe based real-time Q-PCR, Genomics and proteomics technologies, 2001, pp. 53-58, vol. 4264, SPIE, Bellingham, WA.
Solinas, Antonio, et al., Duplex Scorpion primers in SNP analysis and FRET applications, Nucleic Acids Research, 2001, pp. 1-9, vol. 29—No. 20, Oxford University Press.
Mhlanga, Musa M., et al., Using Molecular Beacons to Detect Single-Nucleotide Polymorphisms with Real-Time PCR, Methods, 2001, pp. 463-471, vol. 25, Elsevier Science.
Whitcombe, David, et al., Detection of PCR products using self-probing amplicons and fluorescence, Nature Biotnoloty, Aug. 1999, pp. 804-807, vol. 17, Nature America Inc.

(Continued)

*Primary Examiner* — Pablo S Whaley
(74) *Attorney, Agent, or Firm* — Mauriel Kapouytian Woods LLP; Liang Huang; Michael Mauriel

(57) ABSTRACT

System and methods for the determination of a copy number of a target genomic sequence; either a target gene or genomic sequence of interest, in a biological sample are described. Various methods utilize a model drawn from a probability density function (PDF) for the assignment of a copy number of a target genomic sequence in a biological sample. Additionally, the methods provide for the determination of a confidence value for a copy number assigned to a sample based on attributes of the sample data. Additionally, various embodiments of an interactive graphical user interface (GUI) may provide an end-user with ready analysis of large sets of data representing a plurality of samples. In various embodiments of an interactive GUI, an end-user may be provided with a synchronized display of tabular and graphical sample data determined by an initial analysis according to a statistical model of a PDF. Such a synchronized display may enable an end-user to readily identify sample data for a subsequent analysis based on user input.

7 Claims, 12 Drawing Sheets

(56) References Cited

OTHER PUBLICATIONS

Isacsson, J., et al., Rapid and specific detection of PCR products using light-up probes, Molecular and Cellular Probes, 2000, pp. 321-328, vol. 14., Academic Press.

Svanvik, Nicke, et al., Free-Probe Fluorescence of Light-up Probes, Journal of American Chemical Society, Jan. 21, 2001, pp. 803-809, vol. 123—iss. 5, American Chemical Society.

Wolffs, Petra, et al., PNA-Based Light-Up Probes for Real-Time Detection of Sequence-Specific PCR Products, BioTechniques, Oct. 2001, pp. 766-771, vol. 31—No. 4.

Tsourkas, Andrew, et al., Structure-function relationships of shared-stem and conventional molecular beacons, Nucleic Acids Research, Aug. 2, 2002, pp. 4208-4215, vol. 30—No. 19, Oxford University Press.

Ricelli, Peter V., et al., Melting studies of dangling-ended DNA hairpins: effects of end length, loop sequence and biotinylation of loop bases, Nucleic Acids Research, Jul. 20, 2002, pp. 4088-4093, vol. 30—No. 18, Oxford University Press.

Zhang, et al., Nucleic Acids Research, 2002, pp. 329-332, vol. 34, Shanghai.

Maxwell, Dustin J., et al., Self-Assembled Nanoparticle Probes for Recognition and Detection of Biomolecules, JACS Articles, Jul. 17, 2002, pp. 9606-9612, vol. 124—No. 32, American Chemical Society.

Broude, Natalia E., Stem-loop oligonucleotides: a robust tool for molecular biology and biotechnology, Trends in Biotechnology, 2002, pp. 249-256, vol. 20—No. 6, Elsevier Science Ltd.

Huang, Weidong, et al., Fluorescence Characteristics of Site-Specific and Stereochemically Distinct Benzo[a]pyrene Diol Epoxide-DNA Adducts as Probes of Adduct Conformation, Chem Res. Toxicol. 2002, pp. 118-126, vol. 15—iss. 2, American Chemical Society.

Yu, C.J., et al., Electronic Detection of Single-Base Mismatches in DNA with Ferrocene-Modified Probes, Journal of the American Chemical Society, 2001, pp. 11155-11161, vol. 123—iss. 45, American Chemical Society.

Huang, Jing, et al., CARAT: A novel method for allelic detection of DNA copy number changes using high density oligonucleotide arrays, BMC Bioinformatics, Feb. 2006, pp. 1-21, vol. 7—Iss. 83.

* cited by examiner

| # | Sample | Target | Reference | Plate ID | Copy Number Calculated | Copy Number Predicted | Confidence | [z-score] |
|---|--------|--------|-----------|----------|------------------------|-----------------------|------------|-----------|
| 9 | NKN22259 | C4L | RNase P | | 3.52 | 4 | <0.50 | 1.14 |
| 10 | NKN22259 | C4L | RNase P | | 3.52 | 3-4 | >0.99 | |
| 11 | NKN22259 | C4L | RNase P | | 3.52 | >=4 | <0.50 | |
| 12 | NKN22259 | C4L | RNase P | | 3.52 | >=3 | >0.99 | |
| 9 | NKN22261 | C4L | RNase P | | 2.96 | 3 | >0.99 | 0.03 |
| 10 | NKN22261 | C4L | RNase P | | 2.96 | 3-4 | >0.99 | |
| 11 | NKN22261 | C4L | RNase P | | 2.96 | 3 | >0.99 | |
| 12 | NKN22261 | C4L | RNase P | | 2.96 | >=3 | >0.99 | |
| 9 | NKN22265 | C4L | RNase P | | 3.88 | 4 | 0.99 | 0.07 |
| 10 | NKN22265 | C4L | RNase P | | 3.88 | 3-4 | >0.99 | |
| 11 | NKN22265 | C4L | RNase P | | 3.88 | >=4 | 0.99 | |
| 12 | NKN22265 | C4L | RNase P | | 3.88 | >=3 | >0.99 | |
| 9 | NKN22283 | C4L | RNase P | | 3.65 | 4 | 0.68 | 0.7 |
| 10 | NKN22283 | C4L | RNase P | | 3.65 | 3-4 | >0.99 | |
| 11 | NKN22283 | C4L | RNase P | | 3.65 | >=4 | 0.69 | |
| 12 | NKN22283 | C4L | RNase P | | 3.65 | >=3 | >0.99 | |

A.
☑ Use copy number bins to estimate confidence
Number of copy number bins: 4 ▶
Bin 1: 1
Bin 2: 2
Bin 3: 3-4
Bin 4: >= 5

B.
☑ Use copy number bins to estimate confidence
Number of copy number bins: 4 ▶
Bin 1: 1
Bin 2: 2
Bin 3: 3
Bin 4: >= 4

C.
☑ Use copy number bins to estimate confidence
Number of copy number bins: 3 ▶
Bin 1: 1
Bin 2: 2
Bin 3: >= 3

FIG. 10

SYSTEM FOR DETERMINING A COPY NUMBER OF A GENOMIC SEQUENCE

CROSS-REFERENCE TO RELATED APPLICATION

This application is a continuation of U.S. application Ser. No. 13/689,374, filed Nov. 29, 2012, and claims the benefit under 35 U.S.C. § 119(e) of U.S. Provisional Patent Application Ser. No. 61/564,503 filed Nov. 29, 2011, each of which disclosure is herein incorporated by reference in its entirety.

FIELD

The field of disclosure relates to systems and methods for the determination of a copy number of a genomic sequence in a biological sample.

BACKGROUND

The polymerase chain reaction (PCR) represents an extensive family of chemistries that have produced numerous types of assays of impact in biological analysis. Accordingly, concomitant to the innovation of assays for this family of chemistries has been the innovation of computational methods matched to the objectives of the various PCR-based assays.

For example, one type of computational method suited to various types of quantitative PCR (qPCR) assays is often referred to as the comparative threshold cycle ($C_t$) method. As one of ordinary skill in the art is apprised, the cycle threshold, $C_t$, indicates the cycle number at which an amplified target genomic sequence; either a gene or genomic sequence of interest, reaches a fixed threshold. A relative concentration of a target genomic sequence; either a gene or genomic sequence of interest, may be determined using $C_t$ determinations for the target genomic sequence, a reference genomic sequence; of which for many qPCR assays may be either an endogenous or exogenous reference genomic sequence, and additionally, a calibrator sequence. After normalizing the $C_t$ data for the target gene sequence and the calibrator gene sequence to the reference gene sequence samples, under the assumption that the efficiencies of the reactions are equal and essentially 100%, one of ordinary skill in the art would recognize the calculation for the comparative $C_t$ method as:

$$X_{N,t}/X_{N,c} = 2^{-\Delta\Delta Ct}; \text{ where}$$

$X_{N,t}/X_{N,c}$=is the relative concentration of the target in comparison to the calibrator; and $\Delta\Delta C_t$=is the normalized difference in threshold cycles for the target and the calibrator.

In practice, the efficiency of the PCR process may not be exactly 100%, as the concentration of genetic material may not double at every cycle. Factors that may affect the efficiency of an amplification reaction may include, for example, reaction conditions such as the difference in the detection limit for the dye used for a target genomic sequence versus the dye for the reference, or in inherent differences in the sequence context of the target genomic sequence and a reference genomic sequence. However, as assays are optimized to ensure the highest efficiencies, any deviations from the assumption of 100% efficiency are generally small. In addition to possible deviations from ideality, there are variations of replicate samples of the same sequence, due to variations contributions in an assay system from both the chemistry and instrumentation.

Accordingly, various embodiments of systems and methods for the determination of a gene copy number according to the present teachings use statistical models of a probability distribution function (PDF) to assign a copy number to a sample in a population of samples, and determine a confidence value to the assignment. Such methods take into account various assay deviations and variations. Unlike the comparative $C_t$ method, or $\Delta\Delta C_t$ method, as it is often referred, various methods for the determination of a gene copy number utilize the information in $\Delta C_t$ determinations of samples, and therefore do not require the use of a calibration sample data.

In various embodiments of systems and methods for the determination of a gene copy number according to the present teachings, various embodiments of an interactive graphical user interface (GUI) may provide an end-user with ready viewing and interactive analysis of large sets of data representing a plurality of samples. In various embodiments of an interactive GUI according to the present teachings, an end-user may be provided with a synchronized display of tabular and graphical sample data. Such a synchronized display may enable an end-user to readily identify sample data for a subsequent analysis based on user input.

BRIEF DESCRIPTION OF THE DRAWINGS

FIG. 10 depicts synchronized user input for sub-distribution population information and tabular sample data for various embodiments of an interactive GUI for the analysis of copy number for a biological sample.

DETAILED DESCRIPTION

Figure 1:
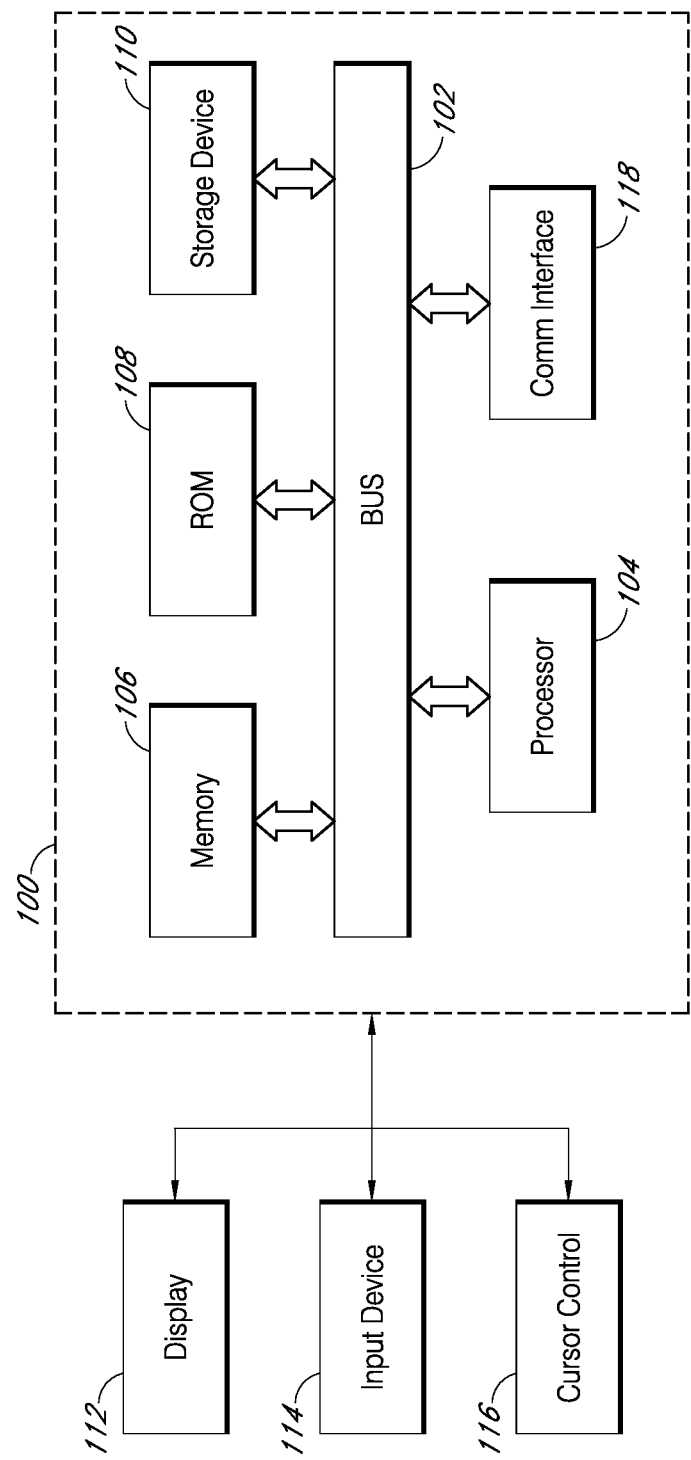
FIG. 1 is a block diagram that illustrates components of an exemplary computer system that may be utilized in the control and interface of a system used for processing biological samples for qPCR.

What is disclosed herein are various embodiments of systems and methods for the determination of a copy number of a target genomic sequence; either a target gene or genomic sequence of interest, in a biological sample. In various embodiments of an interactive GUI according to the present teachings, a synchronized display of tabular and graphical sample data may enable an end-user to readily and effectively view and analyze large sets of sample data. According to the present teachings, various embodiments of an interactive GUI may display synchronized graphical and tabular results for each sample in a plurality of samples based on a model drawn from a probability density function (PDF). In various embodiments of an interactive GUI according to the present teachings, such a graphical display may include a probability density scatter plot, which allows an end-user to view and query a sample in a set of samples in a discrete interval or bin of a probability density scatter plot. Additionally, various embodiments provide for the determination of a confidence value for a copy number assigned to a sample based on attributes of the sample data. Accordingly, a confidence value so determined may provide for an independent evaluation of the assigned copy number generated using a PDF model. Various embodiments of an interactive GUI according to the present teachings may provide for end-user input that includes selection of groupings of sub-distributions in PDF in order to address potential issues of low confidence values for samples falling in copy number sub-distributions having, for example, but not limited by, high sample variability.

The type of assay that is used to provide the data for various embodiments of methods for the determination of a copy number is known to one of ordinary skill in the art as the real-time quantitative polymerase chain reaction (real-time qPCR), in which nucleic acid present in a sample may be amplified.

According to various embodiments, the term "amplified", "amplifying", "amplification" and related terms may refer to any process that increases the amount of a desired nucleic acid. Any of a variety of known amplification procedures may be employed in the present teachings, including PCR (see for example U.S. Pat. No. 4,683,202), as well as any of a variety of ligation-mediated approaches, including LDR and LCR (see for example U.S. Pat. Nos. 5,494,810, 5,830, 711, 6,054,564). Some other amplification procedures include isothermal approaches such as rolling circle amplification and helicase-dependent amplification. One of skill in art will readily appreciate a variety of possible amplification procedures applicable in the context of the present teachings. For example, in some embodiments, the amplification may comprise a PCR comprising a real-time detection, using for example a labeling probe.

The term "labeling probe" generally, according to various embodiments, refers to a molecule used in an amplification reaction, typically for quantitative or real-time PCR analysis, as well as end-point analysis. Such labeling probes may be used to monitor the amplification of the target polynucleotide. In some embodiments, oligonucleotide probes present in an amplification reaction are suitable for monitoring the amount of amplicon(s) produced as a function of time. Such oligonucleotide probes include, but are not limited to, the 5'-exonuclease assay TaqMan® probes described herein (see also U.S. Pat. No. 5,538,848), various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355, 421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor® probes (U.S. Pat. No. 6,548,250), stem-loop and duplex Scorpion™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589, 250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology 17:804-807; Isacsson et al., 2000, Molecular Cell Probes 14:321-328; Svanvik et al., 2000, Anal Biochem. 281:26-35; Wolffs et al., 2001, Biotechniques 766:769-771; Tsourkas et al., 2002, Nucleic Acids Research 30:4208-4215; Riccelli et al., 2002, Nucleic Acids Research 30:4088-4093; Zhang et al., 2002 Shanghai 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Labeling probes can also comprise black hole quenchers (Biosearch), Iowa Black (IDT), QSY quencher (Molecular Probes), and Dabsyl and Dabcel sulfonate/carboxylate Quenchers (Epoch). Labeling probes can also comprise two probes, wherein for example a fluorophore is on one probe, and a quencher on the other, wherein hybridization of the two probes together on a target quenches the signal, or wherein hybridization on target alters the signal signature via a change in fluorescence. Labeling probes can also comprise sulfonate derivatives of fluorescein dyes with a sulfonic acid group instead of the carboxylate group, phosphoramidite forms of fluorescein, phosphoramidite forms of CY 5 (available for example from Amersham). In some embodiments, intercalating labels are used such as ethidium bromide, SYBR® Green I (Molecular Probes), and PicoGreen® (Molecular Probes), thereby allowing visualization in real-time, or end point, of an amplification product in the absence of a labeling probe.

As will be discussed in more detail subsequently, various embodiments of systems and methods may utilize detector signal data collected for a plurality of samples for a copy number assay. Such signals may be stored in a variety of computer readable media. In various embodiments according to the present teachings, a computer program product may be provided, which may include a tangible computer-readable storage medium whose contents include a program with instructions that when executed on a processor perform a method for providing an end-user with the ability to sequentially and rapidly analyze and evaluate the sample data.

FIG. 1 is a block diagram that illustrates a computer system 100 that may be employed to carry out processing functionality, according to various embodiments, upon which embodiments of the present teachings may be implemented. Computing system 100 can include one or more processors, such as a processor 104. Processor 104 can be implemented using a general or special purpose processing engine such as, for example, a microprocessor, controller or other control logic. In this example, processor 104 is connected to a bus 102 or other communication medium.

Further, it should be appreciated that a computing system 100 of FIG. 1 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 100 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 100 may include bus 102 or other communication mechanism for communicating information, and processor 104 coupled with bus 102 for processing information.

Computing system 100 also includes a memory 106, which can be a random access memory (RAM) or other dynamic memory, coupled to bus 102 for storing instructions to be executed by processor 104. Memory 106 also may be used for storing temporary variables or other intermediate information during execution of instructions to be executed by processor 104. Computing system 100 further includes a read only memory (ROM) 108 or other static storage device coupled to bus 102 for storing static information and instructions for processor 104.

Computing system 100 may also include a storage device 110, such as a magnetic disk, optical disk, or solid state drive (SSD) are provided and coupled to bus 102 for storing information and instructions. Storage device 110 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, and/or data.

In alternative embodiments, storage device 110 may include other similar instrumentalities for allowing computer programs or other instructions or data to be loaded into computing system 100. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 110 to computing system 100.

Computing system 100 can also include a communications interface 118. Communications interface 118 can be used to allow software and data to be transferred between computing system 100 and external devices. Examples of communications interface 118 can include a modem, a network interface (such as an Ethernet or other NIC card), a communications port (such as for example, a USB port, a RS-232C serial port), a PCMCIA slot and card, Bluetooth, and the like. Software and data transferred via communications interface 118 are in the form of signals which can be electronic, electromagnetic, optical or other signals capable of being received by communications interface 118. These signals may be transmitted and received by communications interface 118 via a channel such as a wireless medium, wire or cable, fiber optics, or other communications medium. Some examples of a channel include a phone line, a cellular phone link, an RF link, a network interface, a local or wide area network, and other communications channels.

Computing system 100 may be in communication through communications interface 118 to a display 112, such as a cathode ray tube (CRT), liquid crystal display (LCD), and light-emitting diode (LED) display for displaying information to a computer user. In various embodiments, computing system 100 may be couple to a display through a bus. An input device 114, including alphanumeric and other keys, is coupled to bus 102 for communicating information and command selections to processor 104, for example. An input device may also be a display, such as an LCD display, configured with touch screen input capabilities. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane. A computing system 100 provides data processing and provides a level of confidence for such data. Consistent with certain implementations of embodiments of the present teachings, data processing and confidence values are provided by computing system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 104 for execution. Such instructions, generally referred to as "computer program code" (which may be grouped in the form of computer programs or other groupings), when executed, enable the computing system 100 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 110. Volatile media includes dynamic memory, such as memory 106. Transmission media includes coaxial cables, copper wire, and fiber optics, including connectivity to bus 102.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 104 for execution. For example, the instructions may initially be carried on magnetic disk of a remote computer. The remote computer can load the instructions into its dynamic memory and send the instructions over a telephone line using a modem. A modem local to computing system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Figure 2:
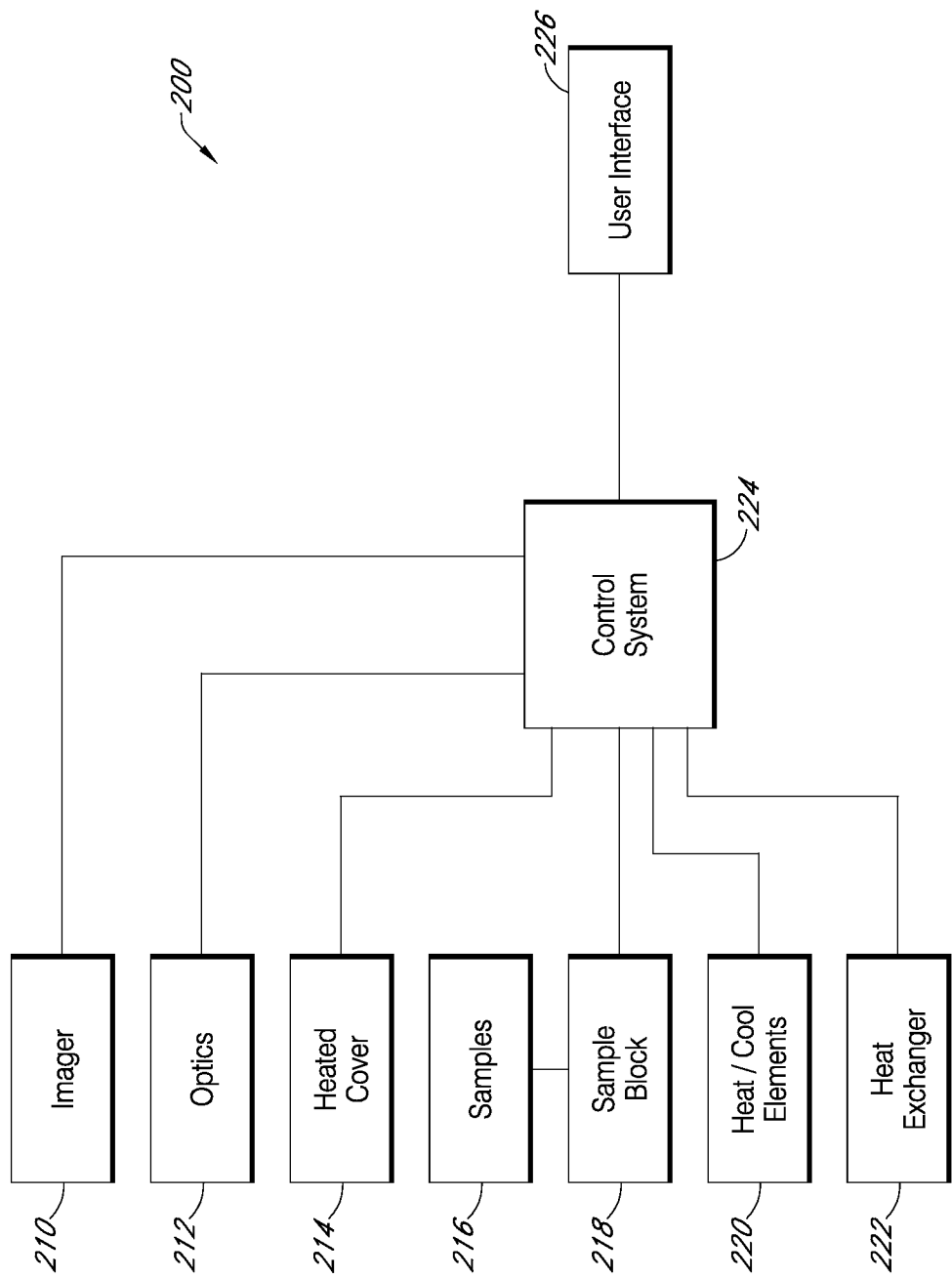
FIG. 2 is a block diagram of an example of some instrument features that may be useful in the processing of biological samples for qPCR.

Various embodiments of systems and methods for the determination of a copy number according to the present teachings may utilize various embodiments of a cycler instrument as depicted in the block diagram shown in FIG. 2. As shown in FIG. 2, a thermal cycling instrument may include a heated cover 214 that is placed over a plurality of samples 216 contained in a sample support device. In various embodiments, a sample support device may be a glass, metal or plastic slide or substrate with a plurality of sample regions, which sample regions have a cover between the sample regions and heated cover 214. Some examples of a sample support device may include, but are not limited by, a multi-well plate, such as a standard microtiter 96-well, a 384-well plate, a micro device capable of processing thousands of samples per analysis or a microcard, or a substantially planar support, such as various microfluidic devices, microcard devices, and micro chip devices fabricated from, for example, but not limited by, a glass, metal or plastic slide or substrate. The sample regions in various embodiments of a sample support device may include depressions, indentations, holes, ridges, and combinations thereof, patterned in regular or irregular arrays formed on the surface of the slide or substrate. Various embodiments of a thermal cycler instrument may include a sample block 218, elements for heating and cooling 220, and a heat exchanger 222.

Various embodiments of a thermal cycler instrument can process multiple samples simultaneously, and may be used in the generation and acquisition of copy number assay data. In FIG. 2, various embodiments of a thermal cycling system 200 provide a detection system for the run time acquisition of signals for each sample in a plurality of biological samples, over the entirety time that a copy number assay is performed. A detection system may have an illumination source that emits electromagnetic energy, and a detector or imager 210, for receiving electromagnetic energy from samples 216 in sample support device.

A control system 224 may be used to control the functions of the detection, heated cover, and thermal block assembly. The control system may be accessible to an end-user through user interface 226 of thermal cycler instrument 200. A computer system 100, as depicted in FIG. 1 may serve as to provide the control the function of a thermal cycler instrument, as well as the user interface function. Additionally, computer system 100 may provide data processing, display and report preparation functions. All such instrument control functions may be dedicated locally to the thermal cycler instrument, or computer system 100 may provide remote control of part or all of the control, analysis, and reporting functions.

As previously described, a large volume of copy number data may be generated as detector signal data is collected over the entirety of a defined time for thermal cycling for each of a large number of samples analyzed during the same run. Given the large volume of data collected over any given copy number analysis, various embodiments of systems and methods of the present teachings provide for embodiments of computer readable media that may generate processed data from initial copy number assay data collected for each sample in a sample support device.

Additionally, various embodiments of systems and methods of the present teachings provide for embodiments of computer readable media that may allow an end-user the flexibility to dynamically analyze large data sets, and selected subsets thereof, using an interactive user interface. Such an interactive user interface may assist an end-user in selection of, for example, but not limited by, a new set of analysis parameters, another method by which the data may be analyzed, the review of data for selected replicate sets of data, as well as the associated statistics for the replicate sets, and the review of which sets of data sets may fall within a selected threshold in comparison to a target set of samples.

Figure 3:
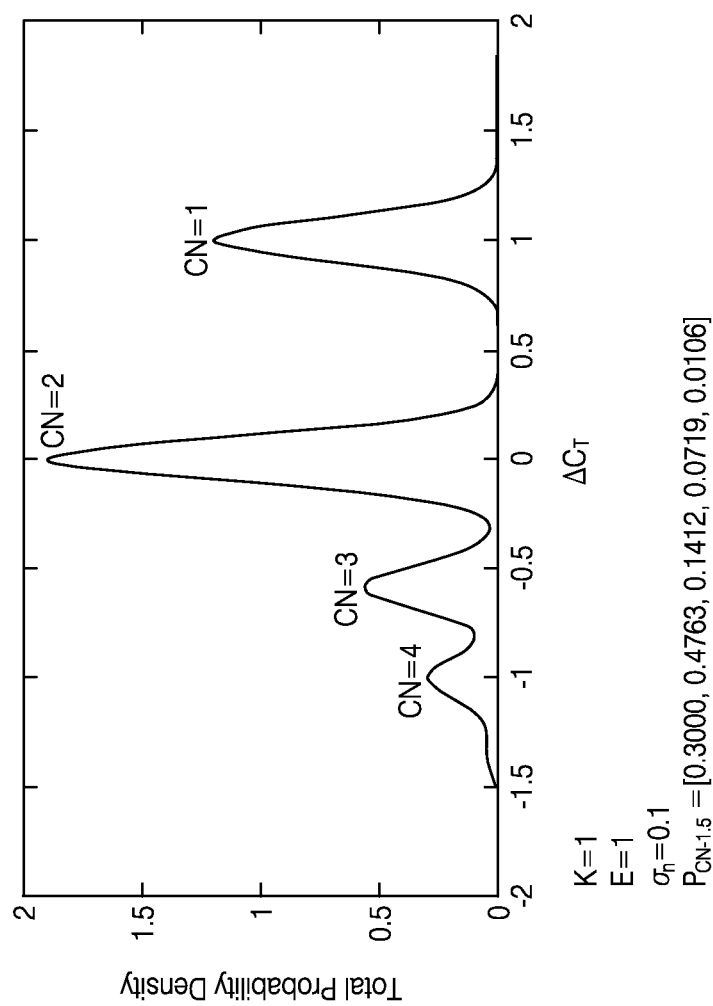
FIG. 3; is an exemplary probability sample frequency population after various embodiments of methods for the determination of gene copy number, which was estimated using a probability density function model based on a normal distribution.

FIG. 3 shows an exemplary determination of copy number for a set of samples using various embodiments of a previously described probability distribution frequency (PDF) statistical method, US 2010/0228496, which is herein incorporated by reference in its entirety.

As is apparent from inspection of FIG. 3, the PDF for this sample set covers the range from copy numbers (CNs) 1 to 5. A characteristic of the exemplary distribution of FIG. 3 is that the separation between the mean of the CN sub-distributions decrease as CN increases. This is a direct consequence of the logarithmic relationship between $\Delta C_t$ and the concentration of genomic material within the context of PCR, as will be discussed in more detail subsequently. As a result of the decreasing separation between sub-distributions with increasing CN, the variability of $\Delta C_t$ values has a larger impact on the resolution of the higher CN values. As measurement variability increases, the average confidence of higher CN calls will decrease much faster than confidence values for lower CN's. Additionally, as will be discussed in more detail subsequently, the relative probability of a copy number, the $P_{CN}$, can influence the confidence value associated with a call. An approximate trend is that the confidence of copy calls increases with increases in the frequency of samples belonging to that CN group. Various embodiments may be used to specify optimum $\Delta C_t$ decision boundaries for CN value assignment. As is depicted in FIG. 3, it is apparent that these boundaries should be placed at the minimum PDF values between the peaks of the PDF since, to either side of these boundaries there is a larger likelihood that the CN corresponds to that of the closer peak in the PDF.

Figure 4:
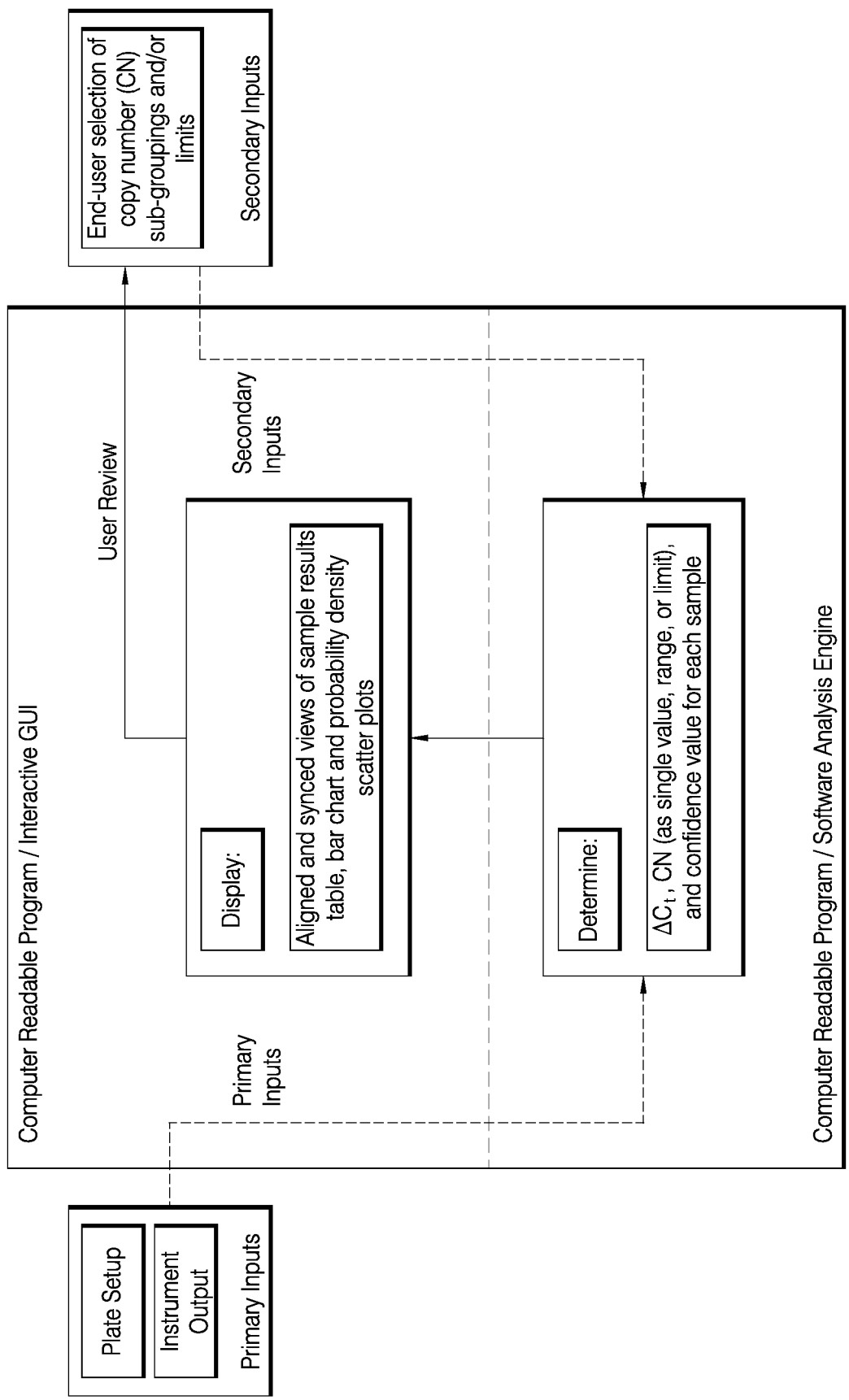
FIG. 4 is representation of an input/output diagram for various embodiments of an interactive GUI for the analysis of copy number for a biological sample.

FIG. 4 depicts an input/output diagram depicting various embodiments of systems and methods for the determination of a copy number. Various embodiments of systems and methods according to the present teachings provide for embodiments an interactive graphical user interface (GUI), which may provide an end-user the ability to dynamically analyze large data sets for copy number determination. As will be discussed in more detail subsequently, and as depicted in FIG. 4, various embodiments of an interactive GUI may provide for end-user input regarding selection of sub-distribution groupings or sub-groupings to be analyzed as a collective group. As previously discussed, the variability of $\Delta C_t$ values may have a larger impact on the resolution of the higher CN values; thereby impacting a confidence value that may be associated with a sample for which a higher CN value has been initially assigned. For various embodiments of an interactive GUI according to the present teachings, an end-user, for example, may wish to know an assignment of CNs to any sample for CNs 1-2, and then anything above CN 2 as a collective group. By way of another example, an end-user may wish to assign copy numbers to samples for CNs 1, 2, 3, and 4, specifically, but may wish to further assign a CN for sample falling within a range of CN 5-7, and then any sample falling above a CN greater than 7. In this regard, for various embodiments of an interactive GUI of the present teachings, an end-user knowing that a confidence value may be low due to a sample for which a single value of CN value may be assigned, can input limits and ranges on copy numbers. In this fashion, end-user input designating grouping of sub-distributions provides for samples to be analyzed as a collective group. As will be discussed subsequently, such a collective group analysis may increase the confidence value associated with the collective group PDF.

Figure 5:
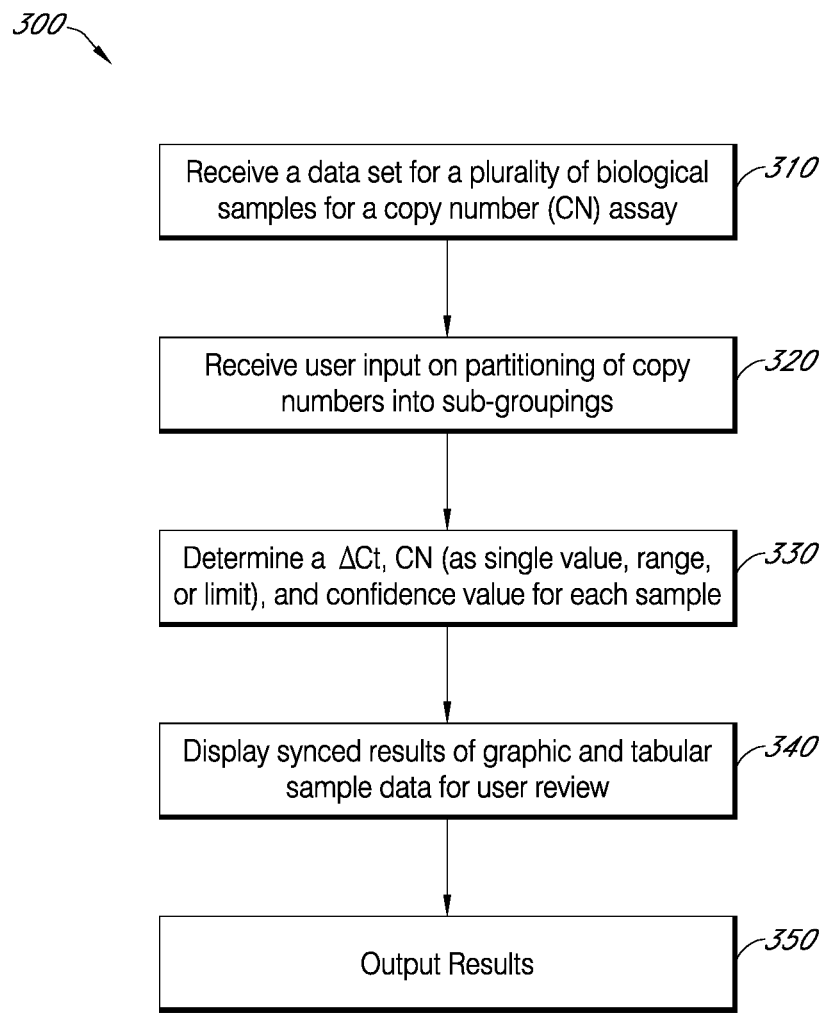
FIG. 5 is a flow chart depicting various embodiments of an interactive GUI for the analysis of copy number for a biological sample.
Figure 6:
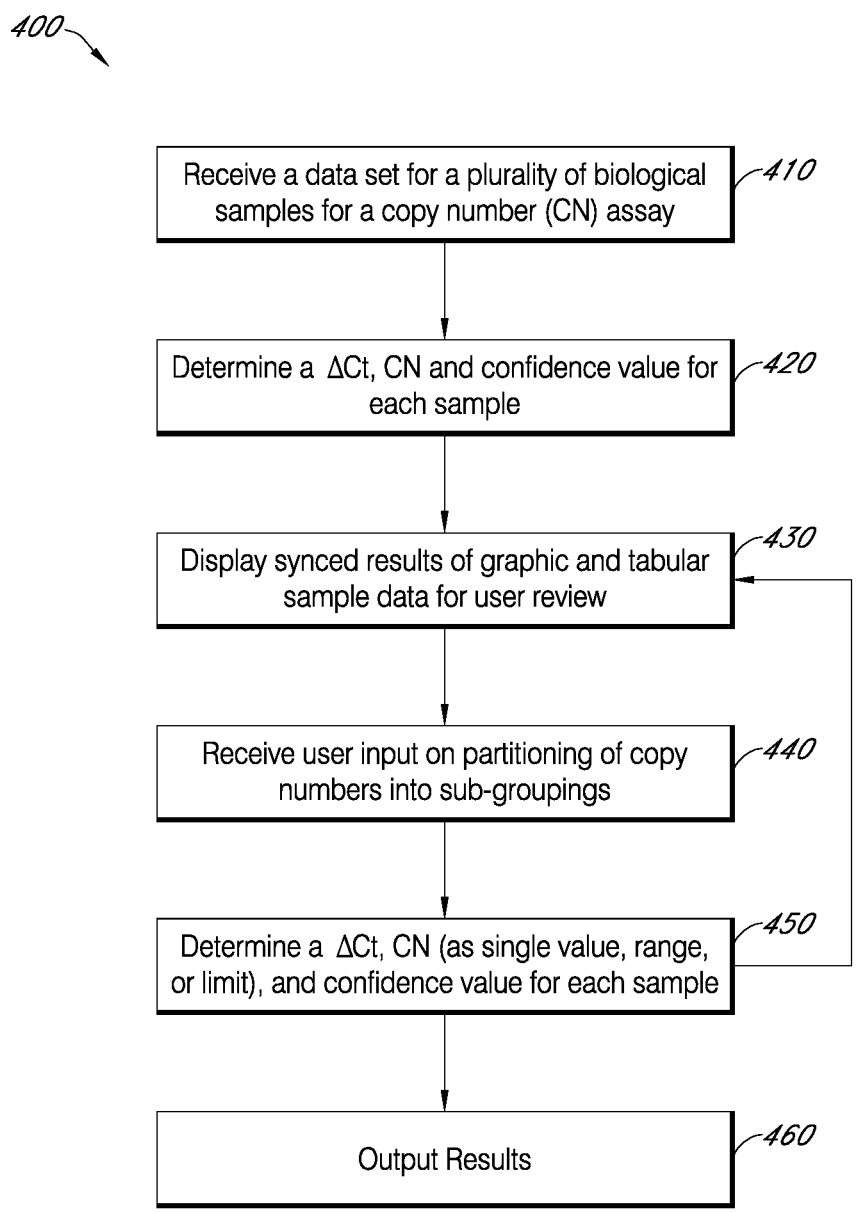
FIG. 6 is a flow chart depicting various embodiments of an interactive GUI for the analysis of copy number for a biological sample.

As depicted in FIG. 4, and depicted in step 310 of FIG. 5 and 410 of FIG. 6, for various embodiments of systems and methods of the present teachings, a set of copy number data for each sample is received by a processor. As indicated in FIG. 4, the data for each sample may include the output from the instrument detector, as well as information about each sample provided in the plate setup created by an end-user. FIG. 5 and FIG. 6 depict various embodiments of systems and methods for the determination of copy number. In step 320 of FIG. 5, an end-user may input information regarding partitioning of copy numbers into sub-distribution groupings or sub-groupings as previously described. Such information may provide ranges and limits for copy numbers. In various embodiments of FIG. 5, and depicted in step 320 of FIG. 5, the user input may be provided before a determination of a CN for a sample is done, as indicated in step 330 of FIG. 5, and before reviewing information provided by a synchronized GUI display of graphic and tabular data is provided to the end-user, as depicted in step 340. In various embodiments of FIG. 6, and as depicted in step 440, the end-user input may be provided after a determination of a CN for a sample is done, as indicated in step 420 of FIG. 6, and after end-user review of information provided by a synchronized GUI display of graphic and tabular data as depicted in step 430 of FIG. 6 is done. As one of ordinary skill in the art is apprised, combinations of various systems and methods as depicted in FIG. 5 and FIG. 6 are possible. For example, but not limited by, an end-user may input the information regarding sub-groupings before a CN determination is done and also after reviewing information provided by a synchronized GUI display of graphic and tabular data. Further, as indicated in FIG. 6 for method 400, review of information provided by a synchronized GUI display of graphic and tabular data and input provided by the end-user may be an iterative process for various embodiments of systems and methods for the determination of a copy number according to the present teachings.

Regarding steps 330 of FIG. 5 for method 300, and step 420 and 450 of FIG. 6 for method 400, determination CN and confidence value may be done based on the determination of $\Delta C_t$ for each sample.

By way of providing an overview of the calculations for $\Delta C_t$ and $\Delta\Delta C_t$ for a copy number assay, the calculation of $\Delta C_t$ values from a data set is based on the equation for the progress of reaction for a PCR assay. It is well know that for a PCR reactions the equation describing the exponential amplification of PCR is given by:

$$X_n = X_o[(1+E_X)^n] \text{ where:} \qquad (EQ. 1)$$

$X_n$=the number of target molecules at cycle n
$X_o$=the initial number of target molecules
$E_X$=the efficiency of the target amplification
n=the number of cycles from that relationship, the concentration of a genomic sequence at the threshold is:

$$X_{Ct,x} = X_o[(1+E_X)^{Ct,x}] = K_X \text{ where:} \qquad (EQ. 2)$$

$X_{Ct,x}$=the number or target molecules at $C_t$
$X_o$=the initial number of target molecules
$E_X$=the efficiency of the target amplification
$C_{t,x}$=the number of cycles at $C_t$
$K_X$=a constant From this it is evident that for a target genomic sequence; either a gene or genomic sequence of interest, the concentration of target formed in the reaction at $C_t$ is a constant K, and therefore characteristic of the reaction. Generally, K may vary for various target genomic sequences, due to a number of reaction variables, such as, for example the reporter dye used in a probe, the efficiency of the probe cleavage, and the setting of the detection threshold. Additionally, as previously described, is generally held that the assumption that the efficiencies of reactions are optimized and essentially the same. Under such conditions and assumptions, it can be shown through the algebraic manipulation of EQ. 2, that normalizing a target genomic sequence of interest of to an endogenous reference reaction at $C_t$ yields the following relationship:

$$X_N = K[(1+E)^{-\Delta Ct}] \text{ where:} \qquad (EQ. 3)$$

$X_N$=is the normalized amount of the target
$\Delta C_t$=is the difference in threshold cycles for the target and endogenous reference genomic sequence Further, it should be noted that for the comparative $C_t$ method, or $\Delta\Delta C_t$ method, that the relative concentration of a target genomic sequence to a calibrator is:

$$X_{N,t}/X_{N,c} = (1+E)^{-\Delta\Delta Ct} \text{ where:} \qquad (EQ. 4)$$

$X_{N,t}/X_{N,c}$=is the relative concentration of the target relative to the calibrator; and
$\Delta\Delta C_t$=is the normalized difference in threshold cycles for the target and the calibrator Then, as previously mentioned, as assays are optimized to ensure a maximum in the reaction efficiency, or an efficiency of 1, then EQ. 4 simplifies to the calculation known to one of ordinary skill in the art for the comparative $C_t$ method previously given:

$$X_{N,t}/X_{N,c}=2^{-\Delta\Delta Ct} \quad \text{(EQ. 5)}$$

According to various embodiments, an equation for copy number as a function of $\Delta C_t$ data generated from qPCR assays having a monomodal PDF sub-distribution for each copy number cn with mean, $\mu_{\Delta Ct}(cn)$, is constrained to be described as:

$$\mu_{\Delta Ct}(cn)=K-\log_{(1+E)}(cn) \text{ where:} \quad \text{(EQ. 6)}$$

$\mu_{\Delta Ct}(cn)=$is the mean of the $\Delta C_t$ sub-distributions as a function of copy number; where cn is a non-zero positive integer K=is a constant; and $\log_{(1+E)}(cn)=$the log to the base (1+E) of copy number cn where E is the efficiency of the PCR amplification of the gene of interest as a result of EQ. 2, where, as previously described, variation in $\Delta C_t$ data around $\mu_{\Delta Ct}(cn)$ may arise within and between samples with the same copy number due to various factors such as, for example, but not limited by, thermal fluctuations in the thermal cycler, and binding behaviors of PCR primers and probes. In various embodiments, an exemplary PDF model may be a normal distribution and, in this case, the full PDF model can be directly characterized by $\mu_{\Delta Ct}(cn)$, K, E, the sample variance, $\sigma$, and the probability of each copy number. Though these parameters directly characterize a PDF using the exemplary normal distribution, it should be understood that any mono-modal distribution PDF may be used, for example, but are not limited by, the Burr, Cauchy, Laplace, and logistic distributions. A central consideration for selection of a distribution function is that the mean of the PDF is constrained to follow EQ. 6. Accordingly, it should be understood that various mono-modal PDFs, such as, but not limited by, the normal, the Burr, Cauchy, Laplace, and logistic distributions may have different sets of parameters that characterize such model PDF distributions.

Additionally, after the set of sample sub-distribution populations included in the sample frequency distribution have copy numbers assigned, thereby assigning copy numbers to every sample included in each sample sub-distribution, a confidence value for every sample in the sample frequency distribution may be determined.

According to various embodiments, the confidence that the assigned copy number is the true copy number within the assumption that the PDF model is accurate may be described most generally by the probability that this is so as described in the following equation:

$$P(cn_{assigned} = cn_{true}) = P(cn_{assigned} | \Delta C_r\text{'s})$$
$$= P(\Delta Ct_r\text{'s} | cn_{assigned})$$
$$P(cn_{assigned}) / P(\Delta Ct_r\text{'s})$$
$$= \frac{\prod\limits_{cn_{assigned}} F(\Delta Ct_r\text{'s}; cn_{assigned})}{\sum\limits_{cn} \prod\limits_{cn} F(\Delta Ct_r\text{'s}; cn)}$$

where $\Delta Ct_r$'s refers to the replicate observations for a given person, and F is the probability distribution function chosen for the sub-distributions that is constrained by requiring that its mean is given by:

$$\mu_{cn}=K-\log_{(1+E)}(cn)$$

$\Pi_{cn}$ is the probability of copy number cn

As exemplary, for various embodiments where F is assumed to be a normal distribution, analyses taken from mathematical statistics can be used to produce the following:

$$P(cn_{assigned} = cn_{true}) = \left[1 + \sum_{cn \neq cn_a} \frac{\prod_{cn}}{\prod_{cn_a}} e^{-\Omega}\right]^{-1} \text{ where} \quad \text{(EQ. 8)}$$

subscript a is shorthand for assigned $\Pi_{cn}$ is the probability of copy number cn $$\Omega \equiv \frac{1}{\sigma^2}\log_{(1+E)}\left(\frac{cn}{cn_a}\right)\left((\hat{\mu}_r - K) + \frac{\log_{(1+E)}(cn_a cn)}{2}\right)$$

$$\hat{\mu}_r = \frac{1}{N_r}\sum_{\substack{all\ replicates\\for\ a\ person}} \Delta Ct_r; \text{ and}$$

$\sigma^2=$the variance of the sub-distributions for each copy number.

According to various embodiments, a confidence value may be determined by first identifying the two sample sub-distributions having the greatest number of samples, and determine the sub-distribution means for the two populations. Such a mean would be the mean of replicate means, or the mean of $\hat{\mu}_r$ given above in EQ. 7. Recalling EQ. 6:

$$\mu_{\Delta Ct}(cn)=K-\log_{(1+E)}(cn) \text{ where:} \quad \text{(EQ. 6)}$$

$\mu_{\Delta Ct}(cn)=$is the mean of a of the $\Delta C_t$ sub-distributions as a function of copy number; where cn is a non-zero integer K=is a constant; and $\log_{(1+E)}(cn)=$the log to the base (1+E) of the copy number of a gene in a sub-distribution of sample distributions, where E is the efficiency of the PCR amplification Then, for various embodiments, $\Delta_{\Delta Ct}(cn)$ is estimated for the two populations having the greatest number of samples, yielding two independent equations, which may be used to solve for the two unknowns, K and E. Additionally, the variance for the mean of sample means, $\sigma_{msm}$ may be determined, as well as $\Pi_{cn}$ the probability of copy number cn. In various embodiments, a distribution of probabilities that the assigned copy number is the true copy number may be generated using the parameters K, E, $\sigma_{msm}$, and $\Pi_{cn}$. According to various embodiments, a Bootstrap technique may be used to generate such a distribution. In various embodiments, once the distribution of the probability measure given by EQ. 7 using the Bootstrap technique is generated, then a confidence level may be selected for the EQ. 7 probability measure. For example, in various embodiments a confidence level assuring that there is a 95% chance that the EQ. 7 probability is equal to or higher than the value determined for this quantity. As will be discussed in more detail subsequently, variables such as the number of samples comprising a sub-population, the copy number, and sample variance may all impact the degree to which high values for the EQ. 7 probability can be achieved.

With respect to 330 of FIG. 5 and 450 of FIG. 6, a confidence interval for a sample associated with a CN interval or limit may be given as follows;

$$P(cn_{m \to n} / \hat{\mu}_r) = \frac{P(\hat{\mu}_r / cn_{m \to n})P(cn_{m \to n})}{P(\hat{\mu}_r)} \quad \text{(EQ. 9)}$$

where $$\hat{\mu}_r = \frac{1}{N_r} \sum_{\substack{\text{all replicates} \\ \text{for a person}}} \Delta Ct_r$$

$$P(\hat{\mu}_r) = \sum_{cn} P(\hat{\mu}_r / cn) P(cn)$$

$$P(cn_{m \to n}) = \sum_{cn = m \to n} \Pi_{cn} \text{ and}$$

$$P(\hat{\mu}_r / cn_{m \to n}) =$$

$$\frac{1}{\sum_{cn=m \to n} \prod_{cn}} \sum_{cn=m \to n} \prod_{cn} N\left(K - L\log(cn), \sqrt{\frac{\sigma_r^2}{N_r} + \sigma_p^2}\right)$$

Then algebraically, the following is derived:

$$P(cn_{m \to n} / \hat{\mu}_r) = \frac{\sum_{cn=m \to n} F_{cn}}{\sum_{cn} F_{cn}} \quad \text{where} \quad \text{(EQ. 10)}$$

$$F_{cn} = \prod_{cn} e^{-(\hat{\mu}_r - K + L\log cn)^2 / \left(2\left(\frac{\sigma_r^2}{N_r} + \sigma_p^2\right)\right)}$$

Figure 7:
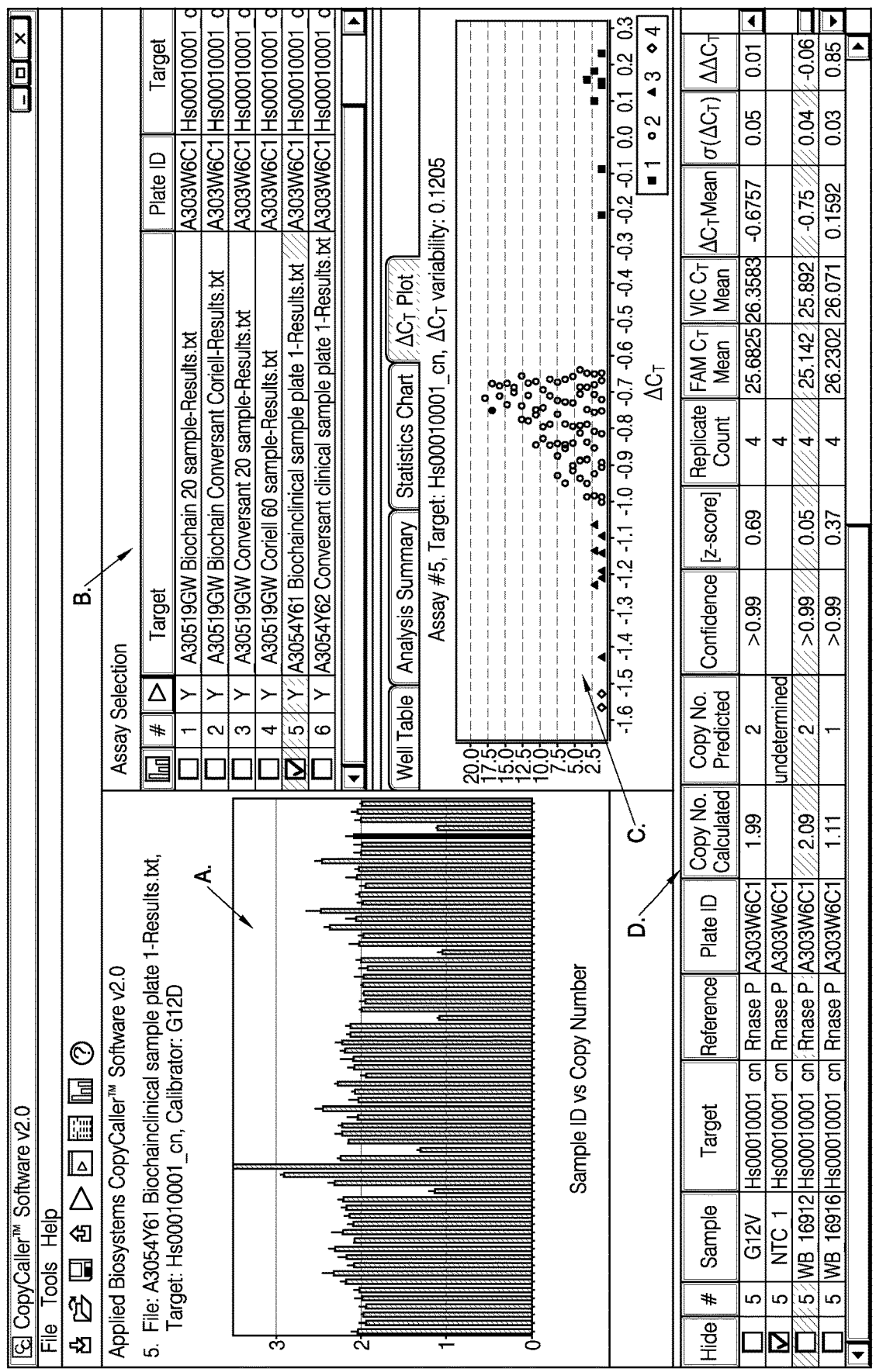
FIG. 7 depicts synchronized graphic and tabular sample results for various embodiments of an interactive GUI for the analysis of copy number for a biological sample.

For step 340 of FIG. 5 of method 300 and step 430 of FIG. 6 of method 400, a synchronized display of graphical and tabular sample data may be provided to an end-user via an interactive GUI. FIG. 7 depicts a synchronized display of graphical and tabular sample data according to various embodiments of systems and methods of the present teachings. In the bar chart of graph A, a single bar is highlighted, as is a single point in the major sub-group of a probability distribution scatter plot C, which is synchronized with for a sample highlighted in assay selection table B and sample results table D. Bar chart A indicates at a glance that the sample selected in sample results table D has been assigned a CN of 2, and additionally the major sub-group in probability distribution plot C is shown to be associated with CN 2 in the legend for probability distribution scatter plot C.

Figure 8:
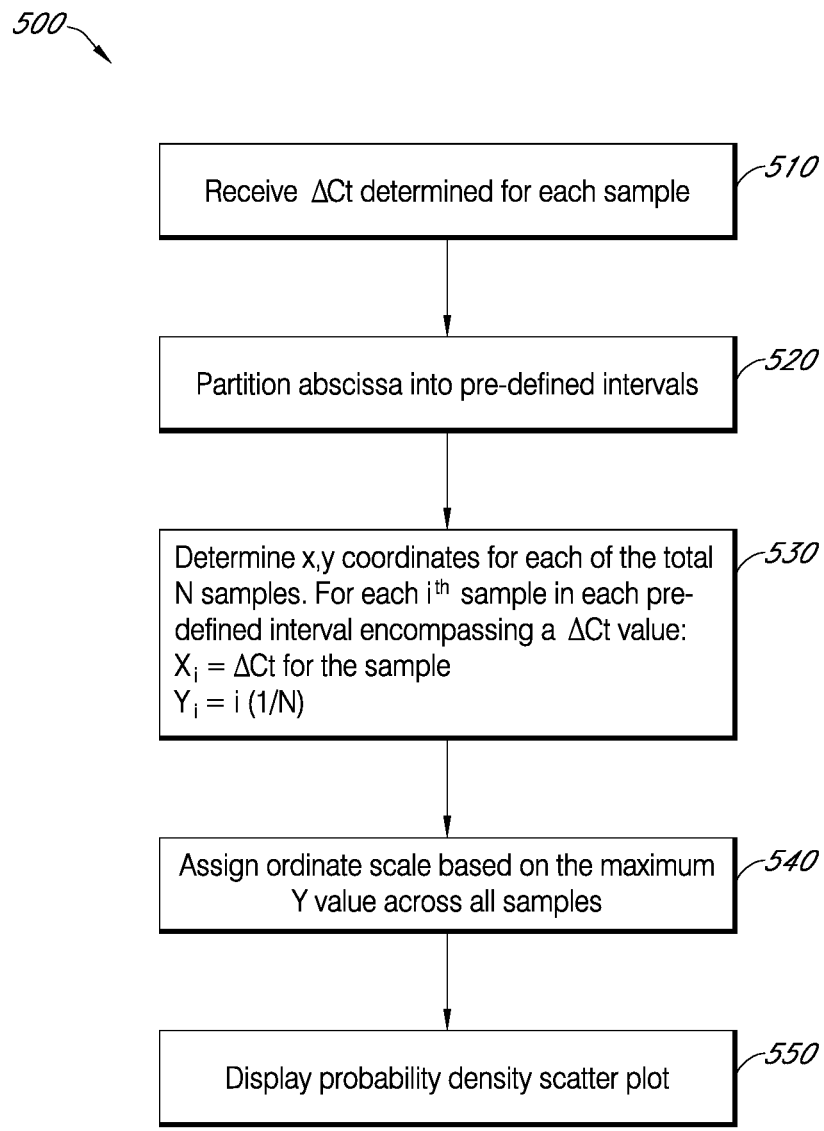
FIG. 8 is a flow chart that depicts various embodiments for plotting and displaying a probability density scatter plot according to the present teachings.
Figure 9A:
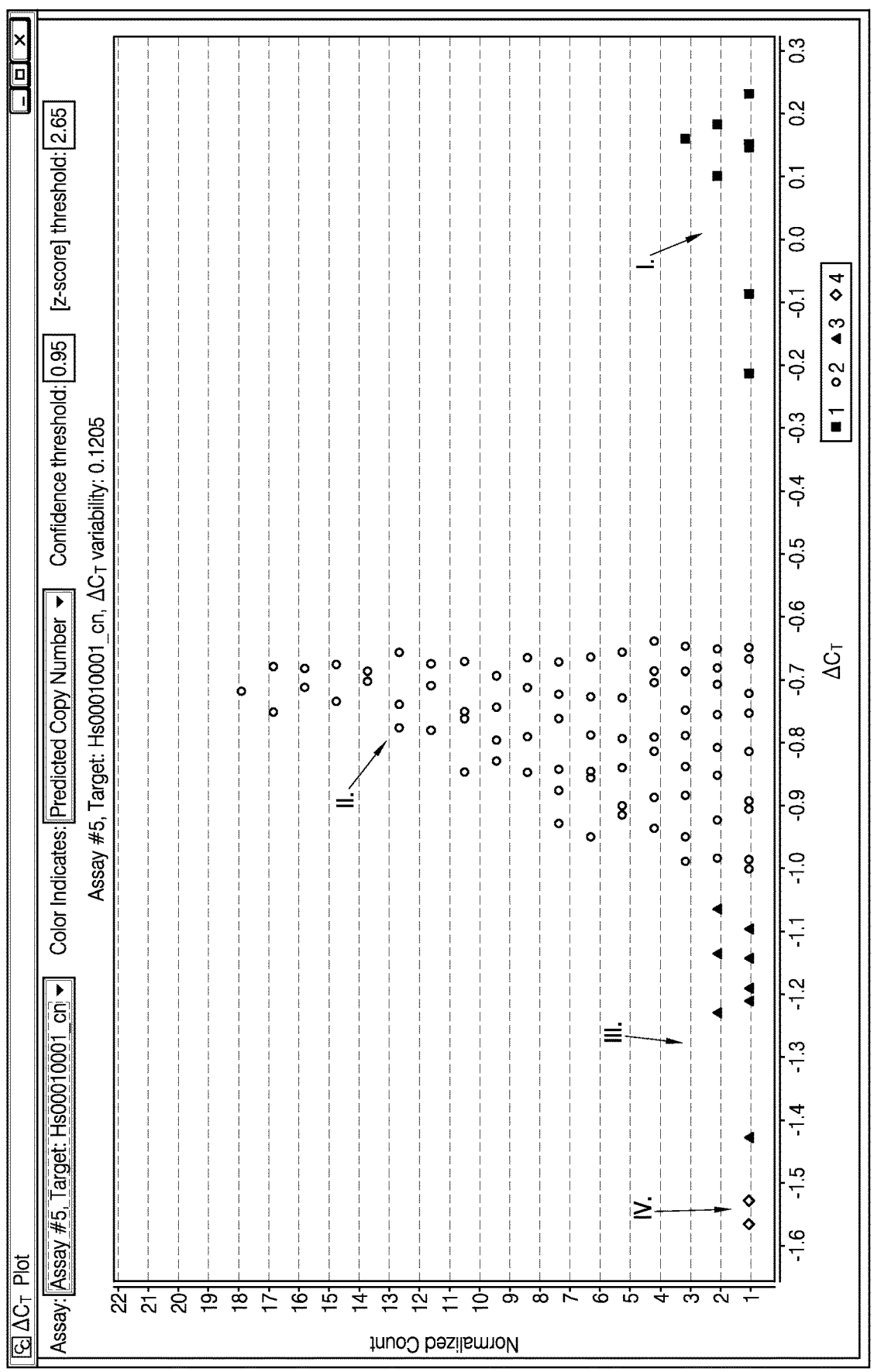
FIG. 9A and FIG. 9B depict embodiments of a probability distribution scatter plot that may be utilized in various embodiments of an interactive GUI for the analysis of a copy number for a biological sample.
Figure 9B:
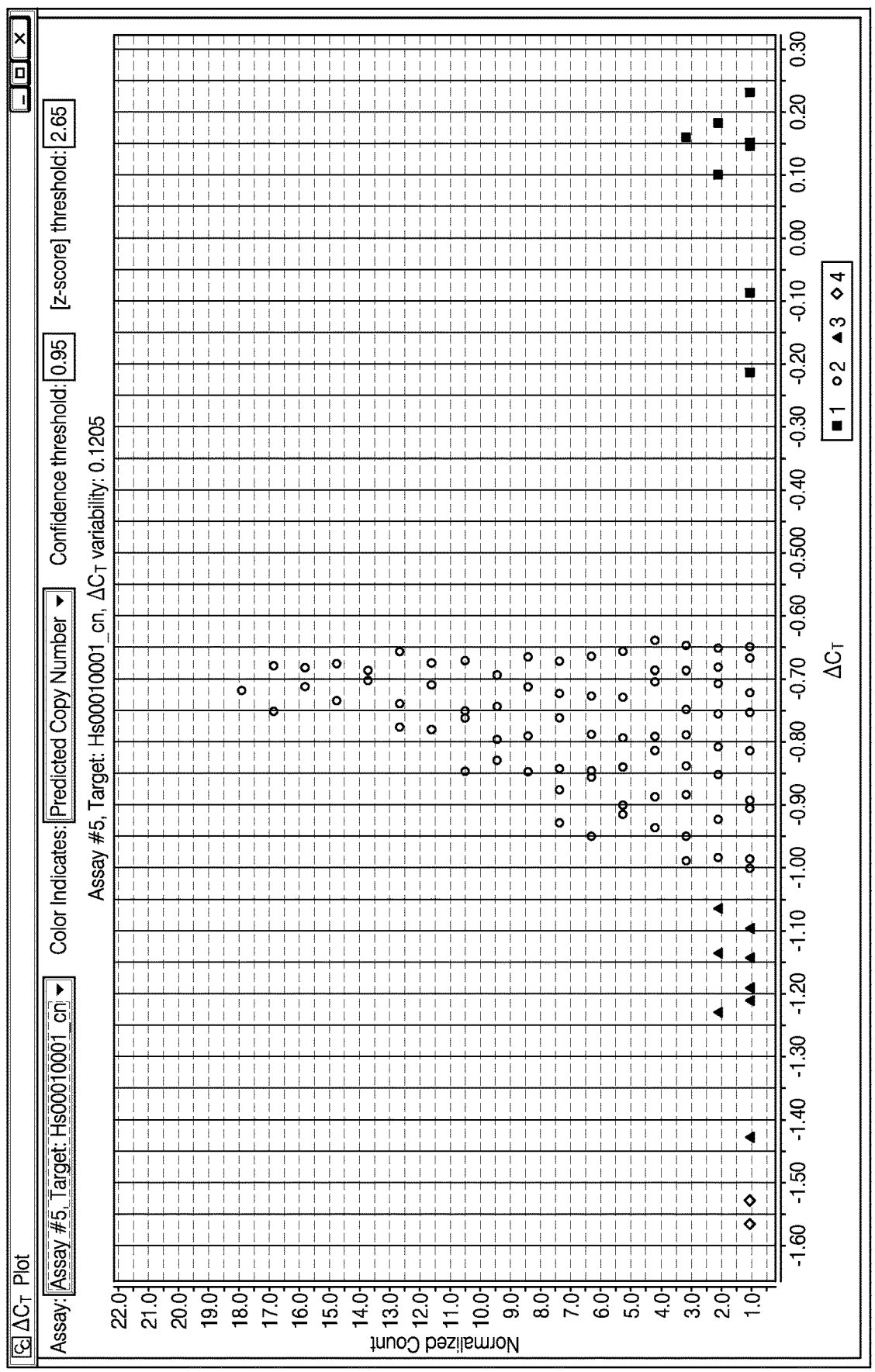

Various embodiments of a probability density scatter plot according to the present teachings are depicted in method 500 of FIG. 8, as well as the plots depicted in FIG. 9A and FIG. 9B. As one of ordinary skill in the art is apprised, various probability density plots, for example, but not limited by, a histogram plot, do not provide an end-user with information about any specific data point in each of a plurality of discrete intervals or bins comprising a probability density plot. One objective of various embodiments of an interactive GUI is to provide an end-user with ready access to a significant amount of information for a plurality of biological samples analyzed in a copy number assay. Such ready access of information provided by a GUI with a synchronized viewing of graphical and tabular data for a sample may greatly assist an end-user with the efficient and timely analysis of such complex data.

In order to enhance the information that can be accessed by an end-user from a probability density plot, a probability density scatter plot was devised. As depicted in method 500 of FIG. 8, $\Delta C_t$ data for each sample is received by a processor at step 510. As one of ordinary skill in the art of probability density plots is apprised, an abscissa may be divided into discrete intervals or bins. Various teachings in the art of probability density plots give guidance on the determination of bin width, or abscissa intervals, suitable for any particular data set. In FIG. 8, step 530 of method 500, a unique X, Y coordinate is determined for every data point representing a $\Delta C_t$ for each sample in a probability density scatter plot. In that regard, in contrast to conventional probability density plots, various embodiments of a probability density scatter plot provide for the display of individual data points. For step 540 of FIG. 8, an ordinate scale of normalized count can be determined using a maximum Y value determined in step 530 of FIG. 8. According to various embodiments of systems and methods of the present teachings, a probability density scatter plot may be displayed in a variety of ways, including as a part of an interactive GUI, as shown in FIG. 7.

As depicted in FIG. 9A, which is the data as shown in FIG. 7, various embodiments of a probability density plot provide ready information about sample distribution, while at the same time providing comparative information regarding each sample. As depicted by the legend for FIG. 9A, samples in group I have been assigned to a CN of 1, samples in group II have been assigned to a CN of 2, samples in group III have been assigned to a CN of 3, and samples in group IV have been assigned to a CN of 4. Additionally, a relative relationship among individual sample data points of discrete intervals or bins is visually provided by embodiments of probability density plots of the present teachings. Moreover, as shown in the synchronized display of an interactive GUI depicted in FIG. 7, an individual sample point of a probability density scatter plot may be readily viewed by an end-user, along with an associated wealth of related information. Though the discrete intervals or bins are not readily visible in an embodiment of a probability density scatter plot depicted in FIG. 9A, the bins used to create the plot are shown in FIG. 9B. FIG. 9B provides clarity for how each sample point in each bin has been plotted according to coordinates determined in step 530 of FIG. 8. Various embodiments of a probability density scatter plot may provide the end-user with the display of bins, as shown in FIG. 9B.

Figure 11:
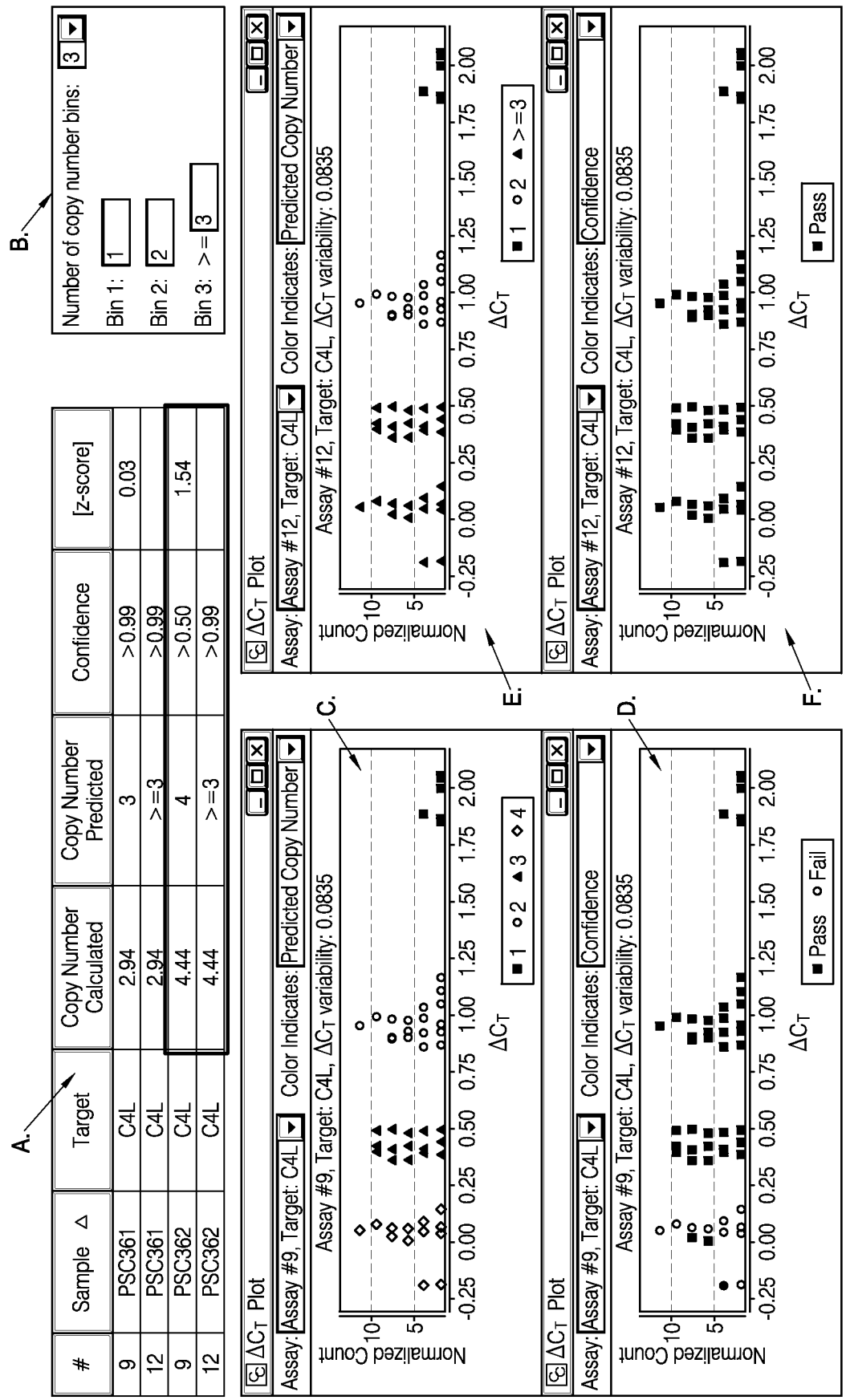
FIG. 11 depicts synchronized graphic and tabular sample results for various embodiments of an interactive GUI for the analysis of copy number for a biological sample.

FIG. 10 and FIG. 11 depict various embodiments of an interactive GUI relating to user input and display, as depicted in steps 320, 340 of method 300 of FIG. 5 and step 440, 430 of method 400 of FIG. 6., respectively In FIG. 10, windows A, B, and C depict various ways that an end-user may select sub-distribution groupings for analysis. According to various embodiments, an end-user may select the number of discrete intervals or bins for a set of biological samples analyzed using a copy number assay. For various embodiments of an interactive GUI, a single value for CN, an interval for CN or a limit for CN may be selected. As depicted in data highlighted in box D, an end-user may inspect the impact to a confidence value generated for a single value of CN assigned, or for any sub-distribution grouping selected by an end-user as shown in windows A, B, and C of FIG. 10. Accordingly, various embodiments of an interactive GUI of the present teaching may provide an end-user a dynamic and efficient tool for assessing sample data generated for a copy number assay.

FIG. 11 depicts a synchronized interactive GUI according various embodiments of systems and methods of the present teachings. As is evident by inspecting table A of FIG. 11, the sample summary indicted in the box is a summary of a single CN value assigned and associated confidence value for a sample in comparison to end-user input of sub-distribution grouping. As seen in window B of FIG. 11, an end-user selection of 3 discrete intervals or bins has been entered for comparison to a single CN value and associated confidence value estimate generated for a set of biological samples analyzed for copy number. In probability density scatter plot C, the data is displayed for an analysis assigning a single value for CN, in which 4 sub-distribution groupings are shown. In probability density scatter plot D, a pass/fail designation for each sample shown in plot C is displayed. As can been seen by inspection, a plurality of samples in sub-distribution groupings above a CN of 3 have failed meeting an acceptable confidence value estimate. In probability density scatter plot E, the data analysis has been run according to the end-user input shown in window B, in which all samples for CN of 3 and above have been grouped together for analysis. As can be seen in probability density scatter plot F, which is a pass/fail designation for each sample shown in plot D, clearly all the failing samples are now associated with a passing confidence value estimate. The synchronized display of various embodiments of an interactive GUI of the present teachings may display the tabular data coordinated with the graphic display. As can be seen in table A of FIG. 11 for a sample designated as PSC362, the numeric values for CN and confidence value estimate can be clearly seen for the assignment of a single value for CN versus the end-user designated sub-distribution groupings.

It should be noted that various embodiments of an interactive GUI according to the present teachings may utilize combinations of color and shape to indicate various attributes of the sample data being displayed, as is shown, for example, FIG. 7 and FIG. 11.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A system for determining a copy number of a genomic sequence in a biological sample utilizing an interactive graphical user interface (GUI), the system comprising:
a thermal cycler instrument configured to amplify a plurality of samples and generate a data set for a copy number assay for the plurality of samples; and
one or more processors in communication with the thermal cycler instrument and configured to:
determine a $\Delta C_t$, a copy number, and a confidence value for each sample in the plurality of samples based on the data set; and
generate, based on the $\Delta C_t$, the copy number, and the confidence value for each sample in the plurality of samples, results for the plurality of samples; and
generate, for display on an electronic display communicatively coupled to the one or more processors, an interactive graphical user interface comprising:
a user input area for receiving user input associated with defining a user-selected set of bins for grouping copy number values;
a first display area including a first probability density scatter plot configured to display results for the plurality of samples grouped according to a first set of bins;
a second display area including a second probability density scatter plot configured to display results for the plurality of samples grouped according to the user-selected set of bins, wherein the user-selected set of bins is different than the first set of bins; and
graphical indications of confidence values associated with a sample's copy number being within a particular bin of the first set of bins and graphical indications of confidence values associated with a sample's copy number being within a particular bin of the user selected set of bins.

2. The system of claim 1 wherein the one or more processors are further configured to generate, for display on the electronic display, an interactive graphical user interface including a synchronized display of the results for the plurality of samples, wherein the synchronized display includes multiple display areas each in a different format, wherein each display area of the multiple display areas displays a visual representation of the plurality of samples as a group along with a visual representation of each sample within the group, wherein each sample is synchronized across each of the multiple display areas, and wherein one display area includes a probability density scatter plot configured to display individual data points.

3. The system of claim 2, wherein each sample is selectable, within each display area of the multiple display areas, the selection of the sample causing an update to each display area of the multiple display areas including highlighting the selected sample and highlighting data related to the selected sample within each display area.

4. The system of claim 2, wherein, in response to user selection of a user-selected sample, the one or more processors are further configured to cause updates of the synchronized display to visually highlight a representation of the user-selected sample in multiple other areas of the interactive interface.

5. The system of claim 2, wherein the multiple display areas include graphical results and tabular results for the plurality of samples modeled using a probability density function (PDF).

6. The system of claim 2, wherein the multiple display areas comprise a probability density scatter plot for the plurality of samples allowing an end-user to view and query a sample in a set of samples in a discrete bin of the probability density scatter plot.

7. The system of claim 1, wherein, in response to user input defining an updated user-selected set of bins, the processor is further configured to cause updates of the graphical indications of confidence values associated with a sample's copy number being within a particular bin of the updated user-selected set of bins.

* * * * *